United States Patent
Xu et al.

(10) Patent No.: US 10,377,992 B2
(45) Date of Patent: *Aug. 13, 2019

(54) BACTERIOPHAGE AND METHODS OF MAKING AND USING

(71) Applicants: Altria Client Services LLC, Richmond, VA (US); Micreos BV, Wageningen (NL)

(72) Inventors: Dongmei Xu, Glen Allen, VA (US); Elisabeth Miller, Chesterfield, VA (US); James Arthur Strickland, Richmond, VA (US); Ujwala Warek, Chester, VA (US); Steven Hagens, Bennekom (NL)

(73) Assignees: Altria Client Services LLC, Richmond, VA (US); Micreos BV, Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/256,228

(22) Filed: Sep. 2, 2016

(65) Prior Publication Data
US 2016/0369245 A1  Dec. 22, 2016

Related U.S. Application Data

(63) Continuation of application No. 14/205,660, filed on Mar. 12, 2014, now Pat. No. 9,433,239.

(60) Provisional application No. 61/791,976, filed on Mar. 15, 2013.

(51) Int. Cl.
| | |
|---|---|
| *C12N 7/00* | (2006.01) |
| *A24B 15/20* | (2006.01) |
| *C07K 14/005* | (2006.01) |
| *C12N 9/36* | (2006.01) |

(52) U.S. Cl.
CPC ............. *C12N 7/00* (2013.01); *A24B 15/20* (2013.01); *C07K 14/005* (2013.01); *C12N 9/2462* (2013.01); *C12Y 302/01017* (2013.01); *C12N 2795/00021* (2013.01); *C12N 2795/00022* (2013.01); *C12N 2795/00031* (2013.01); *C12N 2795/12031* (2013.01)

(58) Field of Classification Search
CPC combination set(s) only.
See application file for complete search history.

(56) References Cited

U.S. PATENT DOCUMENTS

| | | | |
|---|---|---|---|
| 4,528,993 A | 7/1985 | Sensabaugh et al. |
| 4,660,577 A | 4/1987 | Sensabaugh et al. |
| 4,848,373 A | 7/1989 | Lenkey et al. |
| 5,204,257 A | 4/1993 | DeBonville et al. |
| 5,372,149 A | 12/1994 | Roth et al. |
| 5,447,836 A | 9/1995 | Wolber et al. |
| 5,660,812 A | 8/1997 | Merril et al. |
| 5,688,501 A | 11/1997 | Merril et al. |
| 5,712,089 A | 1/1998 | Borrebaeck et al. |
| 5,723,330 A | 3/1998 | Rees et al. |
| 5,766,892 A | 6/1998 | Merril et al. |
| 5,811,093 A | 9/1998 | Merril et al. |
| 5,914,240 A | 6/1999 | Sanders |
| 5,958,675 A | 9/1999 | Wicks et al. |
| 6,027,930 A | 2/2000 | Borrebaeck et al. |
| 6,056,954 A | 5/2000 | Fischetti et al. |
| 6,090,541 A | 7/2000 | Wicks et al. |
| 6,121,036 A | 9/2000 | Ghanbari et al. |
| 6,190,856 B1 | 2/2001 | Li |
| 6,238,661 B1 | 5/2001 | Fischetti et al. |
| 6,248,324 B1 | 6/2001 | Fischetti et al. |
| 6,254,866 B1 | 7/2001 | Fischetti et al. |
| 6,264,945 B1 | 7/2001 | Fischetti et al. |
| 6,265,169 B1 | 7/2001 | Cortese et al. |
| 6,277,399 B1 | 8/2001 | Fischetti et al. |
| 6,326,002 B1 | 12/2001 | Fischetti et al. |
| 6,335,012 B1 | 1/2002 | Fischetti et al. |
| 6,395,504 B1 | 5/2002 | Trudil |
| 6,432,444 B1 | 8/2002 | Fischetti et al. |
| 6,436,661 B1 | 8/2002 | Adams et al. |
| 6,448,083 B1 | 9/2002 | Larocca et al. |
| 6,555,331 B1 | 4/2003 | Hyman et al. |
| 6,635,238 B2 | 10/2003 | Delisle |
| 6,685,937 B2 | 2/2004 | Fischetti et al. |
| 6,699,701 B1 | 3/2004 | Sulakvelidze et al. |
| 6,737,079 B2 | 5/2004 | Fischetti et al. |
| 6,759,229 B2 | 7/2004 | Schaak |
| 6,783,930 B1 | 8/2004 | Pelletier et al. |
| 6,896,882 B2 | 5/2005 | Ramachandran et al. |
| 6,919,075 B1 | 7/2005 | Soloman et al. |
| 6,936,244 B2 | 8/2005 | Fiochetti et al. |

(Continued)

OTHER PUBLICATIONS

Han, Jing, et al. "Bacterial populations associated with smokeless tobacco products." Applied and environmental microbiology 82.20 (2016): 6273-6283.*

Ozawa, H., et al. "Bacteriophage P4282, a parasite of Ralstonia solanacearum, encodes a bacteriolytic protein important for lytic infection of its host." Molecular genetics and genomics 265.1 (2001): 95-101.*

Schmelcher, M., et al., 2012. "Bacteriophage endolysins as novel antimicrobials." Future microbiology 7 (10): 1147-1171.*

Han, Jing, et al. "Bacterial populations associated with smokeless tobacco products." Applied and environmental microbiology 82.20 (2016): 6273-6283 (Year: 2016).*

(Continued)

*Primary Examiner* — Weihua Fan
(74) *Attorney, Agent, or Firm* — Arnold & Porter Kaye Scholer LLP

(57) ABSTRACT

Bacteriophage are provided, and methods of making and using the bacteriophage also are provided. The bacteriophage can be provided in a tobacco product, where the bacteriophage reduces the number of viable bacteria in the tobacco product and includes a nucleic acid sequence encoding an endolysin having at least 95% sequence identity to the nucleic acid sequence shown in SEQ ID NO: 1 or to the amino acid sequence shown in SEQ ID NO: 2.

11 Claims, 6 Drawing Sheets
Specification includes a Sequence Listing.

(56) References Cited

U.S. PATENT DOCUMENTS

| | | |
|---|---|---|
| 6,942,858 B1 | 9/2005 | Ghanbari et al. |
| 6,955,893 B2 | 10/2005 | Delisle |
| 7,063,837 B2 | 6/2006 | Fischetti et al. |
| 7,087,226 B2 | 8/2006 | Ramachandran et al. |
| 7,128,916 B2 | 10/2006 | March |
| 7,141,241 B2 | 11/2006 | Fischetti et al. |
| 7,169,408 B2 | 1/2007 | Fischetti et al. |
| 7,244,612 B2 | 7/2007 | Goodridge |
| 7,276,332 B2 | 10/2007 | Goodridge |
| 7,332,307 B2 | 2/2008 | Carlton et al. |
| 7,459,272 B2 | 12/2008 | Morris et al. |
| 7,588,929 B2 | 9/2009 | Bujanover |
| 7,632,637 B1 | 12/2009 | Boss et al. |
| 7,687,069 B2 | 3/2010 | Fischetli et al. |
| 7,694,686 B2 | 4/2010 | Breslin et al. |
| 7,951,579 B2 | 5/2011 | Hargis et al. |
| 7,985,573 B2 | 7/2011 | Yacoby et al. |
| 8,003,323 B2 | 8/2011 | Morris et al. |
| 8,092,990 B2 | 1/2012 | Voorhees |
| 2004/0118422 A1 | 6/2004 | Lundin et al. |
| 2010/0116281 A1 | 5/2010 | Marshall et al. |
| 2010/0203180 A1 | 8/2010 | Yoon et al. |

OTHER PUBLICATIONS

Ozawa, H., et al. "Bacteriophage P4282, a parasite of Ralstonia solanacearum, encodes a bacteriolytic protein important for lytic infection of its host." Molecular genetics and genomics 265.1 (2001): 95-101. (Year: 2001).*

Schmelcher, M., et al., 2012. "Bacteriophage endolysins as novel antimicrobials." Future microbiology 7 (10): 1147-1171 (Year: 2012).*

Friedberg, I. "Automated protein function prediction—the genomic challenge." Briefings in bioinformatics 7.3 (2006): 225-242 (Year: 2006).*

Rigden, et al., "Amidase domains from bacterial and phage autolysins define a family of γ-d, l-glutamate-specific amidohydrolases." Trends in biochemical sciences 28.5 (2003): 230-234 (Year: 2003).*

Ozawa et al (Molecular genetics and genomics 265.1 (2001): 95-101) (Year: 2001).*

Dorval-Couchesne et al., "Production and Application of Bacteriophage and Bacteriophage-Encoded Lysins," *Recent Patents on Biotechnology*, 2009, 3:37-45.

GenBank Accession No. EHR86787.1.

GenBank Accession No. YP_004149412.1.

GenBank Accession No. ZP_06751371.1.

Hawtrey et al., "Isolation, Characterization, and Annotation: The Search for Novel Bacteriophage Genomes," *The Journal of Experimental Secondary Science*, 2012, 1-9.

Hendrix et al., "Evolutionary relationships among diverse bacteriophages and prophages: all the world's a phage," *PNAS USA*, 1999, 96:2192-7.

International Preliminary Report on Patentability in International Application No. PCT/US2014/024432, dated Jul. 7, 2015, 10 pages.

International Search Report and Written Opinion in International Application No. 2014/024432, dated Nov. 3, 2014, 18 pages.

Invitation to Pay Fees in International Application No. PCT/US2014/024432, dated Sep. 15, 2014, 8 pages.

Ozawa et al., "Bacteriophage P4282, a parasite of Ralstonia solanacearum, encodes a bacteriolytic protein important for lytic infection of its host," Molecular Genetics and Genomics, 2001, 265.1: 95-101.

Pope et al., "Expanding the Diversity of Mycobacteriophages: Insights into Genome Architecture and Evolution," *PLoS One*, Jan. 2011, 6(1):1-20.

Seeley and Primrose, "A Review: The isolation of bacteriophages from the environment," *J. Applied Bacteriology*, 1982, 53:1-17.

Son et al., "Antibacterial and biofilm removal activity of a podoviridae *Staphylococcus aureus* bacteriophage SAP-2 and a derived recombinant cell-wall-degrading enzyme," Applied Microbiology and Biotechnology, Dec. 2009, 86(5):1439-1449.

Takac, "Functional analysis of the lysis genes of *Staphylococcus aureus* phage P68 in *Escherichia coli*," Microbiology, Jul. 2005, 151(7):2331-2342.

Tanaka et al., "Control of tobacco bacterial wilt by an avirulent strain of Pseudomonas solanacearum M4S and its bacteriophage," Ann. Phytopath. Soc. Japan, Jan. 1990, 56:243-246.

Tso, "Seed to Smoke," Tobacco, Production, Chemistry and Technology, Davis & Nielsen, eds., 1999, Chapter 1, 33 pages.

Vybiral et al., "Complete nucleotide sequence and molecular characterization of two lytic *Staphylococcus aureus* phages: 44AHJD and P68," FEMS Microbiology Letters, Feb. 2003, 219(2):275-283.

\* cited by examiner

BACTERIOPHAGE AND METHODS OF MAKING AND USING

CROSS REFERENCE TO RELATED APPLICATIONS

This application is a continuation of U.S. application Ser. No. 14/205,660, filed on Mar. 12, 2014, which claims the benefit of priority under 35 U.S.C. § 119(e) to U.S. Application No. 61/791,976 filed on Mar. 15, 2013. The prior application is incorporated herein by reference in its entirety.

TECHNICAL FIELD

This disclosure generally relates to bacteriophage and methods of using the bacteriophage.

BACKGROUND

Bacteriophage destroy bacteria but are harmless to humans. They are strain and, usually, species specific, and they are abundant in nature, in foods, and in the intestinal tract of animals. Bacteriophage are about 100 times smaller than bacteria, and they leave no ecological footprint. Bacteriophage are generally recognized as safe (GRAS).

The lytic lifecycle of bacteriophage typically includes adsorption to a bacterial cell, infection, which includes injecting their nucleic acid into the bacterial cell, replication, maturation, and assembly of bacteriophage inside the bacterial cell. The lytic lifecycle culminates in lysis of the bacterial cell to release all the progeny bacteriophage.

Bacteriophage can be used as an alternative to antibiotics in the battle against bacteria. LISTEX is an example of a commercially available bacteriophage that infects and causes lysis of *Listerial monocytogenes*.

SUMMARY

This disclosure describes bacteriophage and methods of making and using the bacteriophage.

In one aspect, an isolated bacteriophage having lytic activity against M4 is provided. Such a bacteriophage includes a nucleic acid sequence encoding an endolysin, wherein the nucleic acid sequence has at least 95% sequence identity to the nucleic acid sequence shown in SEQ ID NO:1. In some embodiments, the nucleic acid sequence has at least 99% sequence identity to the nucleic acid sequence shown in SEQ ID NO:1. In some embodiments, the nucleic acid sequence has the sequence shown in SEQ ID NO:1. In some embodiments, the endolysin encoded by the nucleic acid sequence has the amino acid sequence shown in SEQ ID NO:2.

In another aspect, an isolated bacteriophage having lytic activity against M4 is provided. Such a bacteriophage includes a nucleic acid sequence encoding an endolysin having at least 95% sequence identity to the amino acid sequence shown in SEQ ID NO:2. In some embodiments, the endolysin has at least 99% sequence identity to the amino acid sequence shown in SEQ ID NO:2. In some embodiments, the endolysin has the amino acid sequence shown in SEQ ID NO:2.

In still another aspect, a method for reducing the number of viable M4 in tobacco is provided. Such a method typically includes contacting tobacco with an effective amount of a composition comprising any of the isolated bacteriophage described herein. In some embodiments, the tobacco is contacted with the bacteriophage composition prior to fermentation of the tobacco. Generally, the method reduces the level of TSNAs in the tobacco.

In yet another aspect, an isolated bacteriophage having lytic activity against *Geobacillus stearothermophilus* is provided.

In another aspect, a method for preventing or reducing the presence of a *Geobacillus*-produced biofilm is provided. Such a method typically includes contacting the biofilm with an effective amount of a composition comprising any of the isolated bacteriophage described herein. In some embodiments, the biofilm is present on tobacco (e.g., reconstituted leaf tobacco) or tobacco solubles. In some embodiments, the biofilm is present in fluid-carrying pipes (e.g., fluid-carrying pipes that carry milk).

In one aspect, tobacco that includes one or more bacteriophages described herein is provided. In some embodiments, the tobacco is aged and cured. In some embodiments, the bacteriophage is any of the bacteriophages described herein. Also provided is a smokeless tobacco product that includes such tobacco. Also provided is a cigarette that includes such tobacco.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF SEQUENCE LISTING

Figure 1:
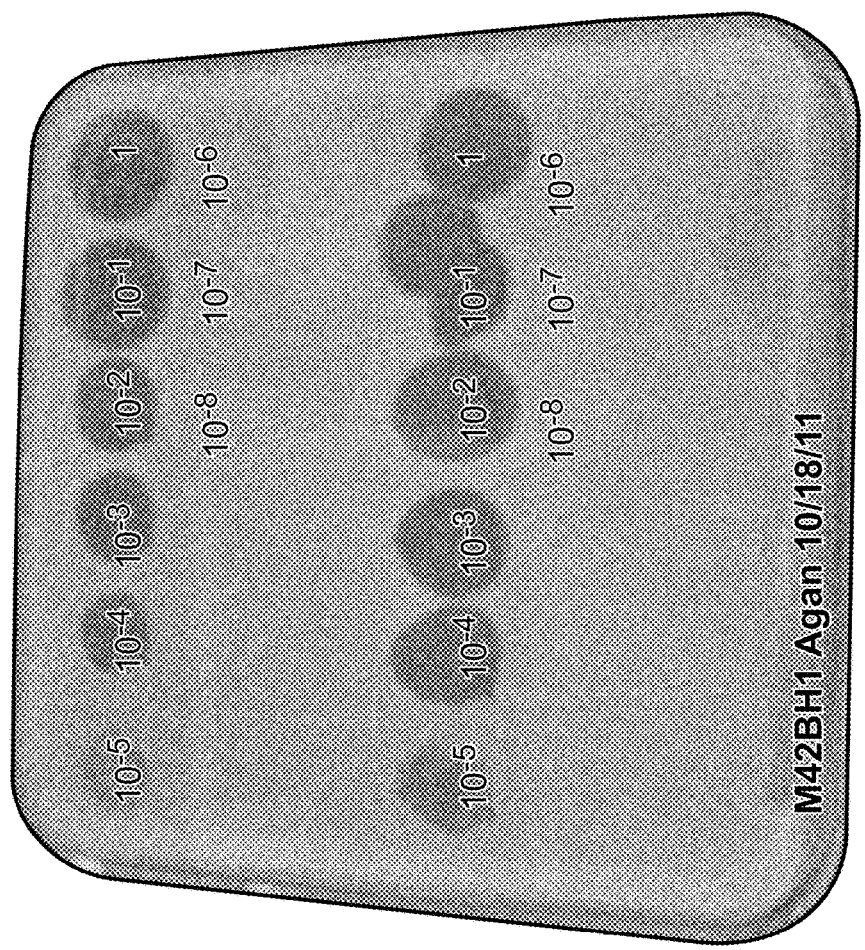
FIG. 1 is a photograph showing the plaques resulting from infection of M4 with serial dilutions of P4 to determine the titer.

SEQ ID NO:1 is the nucleic acid sequence of the endolysin gene from P4.
SEQ ID NO:2 is the amino acid sequence of the endolysin from P4.

DETAILED DESCRIPTION

A number of bacteria are present on tobacco, while growing in the field or after harvest, and at various stages of processing. Some of those bacteria are beneficial and, for example, contribute to the flavor profiles of tobacco, while some of those bacteria are undesirable and, for example, damage the tobacco and contribute to unwanted tobacco-specific nitrosamines (TSNAs).

For example, there are several bacteria present in tobacco that negatively affect the shelf life of tobacco products, designated bacterial strains M3 and M4. In addition, there are several bacteria that are involved in TSNA formation during processing and product shelf life, designated bacterial strains M5 and M6. Further, at least one unwanted bacteria present on reconstituted leaf (RL) results in a biofilm, which causes holes in the RL and results in significant loss of yield. The primary genus of bacteria in the biofilm (about 95%) was identified as *Geobacillus*.

Bacteriophage Compositions

A number of isolated bacteriophage are provided herein, as well as progeny thereof. As used herein with respect to bacteriophage, "isolated" refers to a bacteriophage that has been separated from the environment in which it is naturally found (e.g., that does not contain a significant amount of other bacteriophage or of the bacterial host). As used herein, "progeny" refers to replicates of a bacteriophage, including descendants of a bacteriophage created by serial passage or other methods known in the art.

In addition to bacteriophage, a bacteriophage composition also can include media, buffers, one or more nutrients, one or more minerals, one or more co-factors, or any other component that is necessary to maintain viability of the bacteriophage. Additionally, components that are not related to the viability of the bacteriophage may be desirable in a bacteriophage composition such as, without limitation, a dye or color marker.

Bacteriophage Nucleic Acids and Polypeptides

Bacteriophage contain endolysins, a generic term for one or more enzymes that are involved in the degradation of the peptidoglycan in the bacterial cell wall, ultimately resulting in lysis of the bacteria. The specificity exhibited by the bacteriophage for a particular bacteria strain is typically attributed to the endolysin(s). Therefore, as described herein, isolated bacteriophage nucleic acids are provided that encode for the endolysins, and the purified endolysin polypeptides also are provided.

The endolysin gene from the P4 bacteriophage has the nucleic acid sequence shown in SEQ ID NO:1 and encodes an endolysin polypeptide having the sequence shown in SEQ ID NO:2.

In addition to the nucleic acid sequence shown in SEQ ID NO: 1, and the polypeptide sequence shown in SEQ ID NO: 2, nucleic acid and polypeptide sequences are provided that differ in sequence from SEQ ID NO: 1 and SEQ ID NO: 2, respectively. For example, nucleic acid sequences having at least 70% sequence identity (e.g., at least 75%, 80%, 85%, 90%, 95%, 99% or 100% sequence identity) to the nucleic acid sequence shown in SEQ ID NO: 1 are provided. Similarly, amino acid sequences having at least 70% sequence identity (e.g., at least 75%, 80%, 85%, 90%, 95%, 99% or 100% sequence identity) to the amino acid sequence shown in SEQ ID NO: 2 are provided.

To calculate the percent sequence identity of two sequences, the first and second sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align differently with other sequences and hence, can have different percent sequence identity values over each aligned region. Two sequences can be aligned to determine percent sequence identity using the algorithm described by Altschul et al. (1997, *Nucleic Acids Res.,* 25:3389-3402), which is incorporated into BLAST (basic local alignment search tool) programs available at ncbi.nlm.nih.gov on the World Wide Web.

With respect to nucleic acids, an "isolated" nucleic acid refers to a nucleic acid that is separated from other nucleic acids that are usually associated with the isolated nucleic acid. Thus, an "isolated" nucleic acid includes, without limitation, a nucleic acid that is free of sequences that naturally flank one or both ends of the nucleic acid in the genome of the organism from which the isolated nucleic acid is derived (e.g., a cDNA or genomic DNA fragment produced by PCR or restriction endonuclease digestion). In addition, an isolated nucleic acid molecule can include an engineered nucleic acid molecule such as a recombinant or a synthetic nucleic acid molecule. With respect to polypeptides, a "purified" polypeptide refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

The nucleic acids described herein (e.g., encoding the bacteriophage endolysin polypeptides) can be introduced into vectors. Vectors, including expression vectors, are commercially available or can be produced by routine molecular biology methods. A vector containing a bacteriophage nucleic acid also can have elements necessary for expression operably linked to the bacteriophage nucleic acid, and a vector further can include sequences such as those encoding a selectable marker (e.g., an antibiotic resistance gene) and/or sequences that can be used in purification of a polypeptide (e.g., 6×His tag).

Elements necessary for expression include nucleic acid sequences that direct and regulate expression of nucleic acid coding sequences such as, for example, promoter sequences. Elements necessary for expression also can include introns, enhancer sequences, response elements, or inducible elements that modulate expression of a nucleic acid. As used herein, operably linked means that an element necessary for expression (e.g., a promoter and/or other regulatory element) is positioned in a vector relative to a nucleic acid coding sequence in such a way as to direct or regulate expression of the nucleic acid coding sequence.

Vectors containing a bacteriophage nucleic acid can be introduced into host cells. Methods of introducing nucleic acids into host cells are known in the art and include, without limitation, calcium phosphate precipitation, electroporation, heat shock, lipofection, microinjection, and viral-mediated nucleic acid transfer. The term "host cell" refers not only to the particular cell but also to the progeny or potential progeny of such a cell. A host cell can be any prokaryotic or eukaryotic cell. For example, nucleic acids can be expressed in bacterial cells such as, without limitation, E. coli, or in insect cells, yeast cells, or mammalian cells such as Chinese hamster ovary (CHO) cells or COS cells. It would be appreciated by those skilled in the art that the natural infection process of bacteriophage can be used to introduce a nucleic acid or nucleic acid vector into a bacterial cell.

Methods of Using Bacteriophage Compositions and Bacteriophage Nucleic Acids and Polypeptides The P4 bacteriophage described herein, or the P4 bacteriophage endolysin nucleic acid or polypeptide described herein, can be used in methods of reducing the number and/or growth of M4 bacteria. For example, tobacco (e.g., moist smokeless tobacco) can be contacted with an effective amount of the P4 bacteriophage described herein, or the P4 bacteriophage endolysin nucleic acids or polypeptides described herein. The moist, smokeless tobacco can be contacted with an effective amount of one or more of the indicated bacteriophage, or an endolysin nucleic acid or polypeptide, prior to, during and/or after fermentation of the tobacco, and/or at the finishing stage.

Briefly, after harvesting, tobacco can be cured using conventional means, e.g., air curing, fire curing, barn curing, sun curing. See, for example, Tso (1999, Chapter I in Tobacco, Production, Chemistry and Technology, Davis & Nielsen, Eds., Blackwell Publishing, Oxford). Optionally, cured tobacco then can be conditioned and/or fermented. Conditioning includes, for example, a heating, sweating or pasteurization step as described in U.S. Publication Nos. 2004/0118422 or 2005/0178398. Fermenting typically is characterized by high initial moisture content, heat generation, and a 10 to 20% loss of dry weight. See, for example, U.S. Pat. Nos. 4,528,993; 4,660,577; 4,848,373; and 5,372,149. Cured or cured and fermented tobacco then can be further processed (e.g., cut, expanded, blended, milled or comminuted).

Contacting tobacco during the processing and finishing of the products with the P4 bacteriophage described herein results in a number of benefits or improvements to the tobacco including, without limitation, a reduction in the level of TSNAs in the tobacco, and an increased shelf-life of the tobacco product. A reduction in the level of TSNAs is defined as a reduction in at least 10% (e.g., at least 15%, 20%, 25%, 30%, 40%, 50% or more) TSNAs in bacteriophage-contacted tobacco relative to tobacco not contacted with bacteriophage. The shelf-life of a tobacco product is increased if the tobacco in the tobacco product maintains its sensory characteristics (e.g., mouth feel, flavor profile, etc.) for a longer period of time than a comparable tobacco product containing tobacco cured and processed under comparable conditions but without bacteriophage (a "control" tobacco product). Under certain circumstances, the shelf life of the tobacco product containing the bacteriophage-contacted tobacco is statistically significantly longer than the shelf-life of a control tobacco product. As used herein, "statistically significantly" refers to a p-value of less than 0.05 (e.g., less than 0.025 or 0.01) using an appropriate measure of statistical significance (e.g., a one-tailed two-sample t-test).

In addition, the Pgeo bacteriophage described herein can be used in methods of reducing the amount and/or growth of G. stearothermophilus on reconstituted leaf (or on any of the tobacco materials used to make reconstituted leaf), which reduces the resulting Geobacillus-produced biofilm on the reconstituted leaf. For example, reconstituted leaf can be contacted with the Pgeo bacteriophage at any point during the process of making the reconstituted leaf or after the reconstituted leaf has been produced. In certain instances, the tobacco material (e.g., tobacco stems, tobacco leaves, tobacco solubles) can be contacted with the Pgeo bacteriophage prior to being used in or made into reconstituted leaf. Contacting reconstituted leaf (or tobacco material prior being made into reconstituted leaf) with the Pgeo bacteriophage described herein reduces the amount of biofilm present on the reconstituted leaf. Since the presence of biofilm results in holes in the reconstituted leaf, the Pgeo-treated reconstituted leaf has fewer holes, which increases yield and decreases waste.

Since biofilm is present in a number of different environments (e.g., hospitals, kitchens, bathrooms, in fluid-carrying pipes (e.g., carrying water, milk, oil, fuel, or sewage), on boat hulls, on plants or trees, in the oral cavities of animals, and/or in paper- or pulp-making facilities), and since at least a portion of this biofilm is Geobacillus-produced biofilm, the Pgeo bacteriophage described herein can be used to reduce or eliminate the biofilm that is present in these different environments.

As used herein, a reduction in the number of viable bacteria means a reduction in the number of bacteria that are alive and capable of, for example, replication. For example, lysed bacteria or bacteria in the process of lysing are not considered viable. The viability of bacteria can be determined using methods routinely used in microbiology. In addition, preventing or reducing the amount of biofilm means that the surface area containing biofilm is reduced or the volume of the biofilm on a surface is reduced relative to a "control" surface that has not been contacted with a bacteriophage. These reductions (i.e., in the number of viable bacteria or the amount of biofilm) in the presence of any of the bacteriophage (or endolysin nucleic acid or polypeptide) described herein are a result of the lytic activity exerted by the bacteriophage (or endolysin nucleic acid or polypeptide) on the bacteria. As used herein, an "effective amount" of a bacteriophage or of an endolysin nucleic acid or polypeptide is an amount that results in lysis of bacteria in an amount or at a rate that is sufficient to reduce the number of viable bacteria or the amount of biofilm present to a desired level.

Methods of Obtaining Bacteriophage Compositions

Methods of obtaining bacteriophage are known in the art. See, for example, Bacteriophages: Methods and Protocols, Volume 1: Isolation, Characterization, and Interactions (Methods in Molecular Biology), Eds, Clokie & Kropinski, 2010, Humana Press; Seeley et al., 1982, J. Applied Bacteriol., 53:1-17; Pope et al., 2011, PLoS ONE, 6:e16329; and Hendrix et al., 1999, PNAS USA, 96:2192-7. Briefly, bacteria of interest (e.g., the target bacteria) are obtained, generally using standard culture methods. Typically, bacteria are cultured in such as way so as to activate the lytic phase of bacteriophage native to the bacteria and cause lysis. Following lysis of the bacteria, the bacteriophage is collected and can be characterized using any number of known methods such as, without limitation, nucleic acid sequencing, electron microscopy, burst size, and/or attachment rate. Bacteriophage also can be described based on their host (i.e., host profiling).

Tobacco Products

Tobacco products for adult tobacco consumers are provided that contain tobacco (e.g., whole leaf, stems, and cut, chopped or comminuted leaf or stem) or reconstituted leaf that has been contacted with one or more bacteriophage (or endolysin nucleic acids or polypeptides). In some instances, the bacteriophage is the P4 bacteriophage described herein.

Under certain circumstances, the tobacco or reconstituted leaf can undergo one or more treatments in order to remove or inactivate the bacteriophage once the amount and/or growth of the respective bacteria has reached an acceptable level. However, since bacteriophage are in the "generally recognized as safe (GRAS)" category, the bacteriophage may be present in the final tobacco product.

In some instances, the tobacco product is a smokeless tobacco product. Representative examples of smokeless tobacco products include, without limitation, chewing tobacco, moist smokeless tobacco, and dry snuff. In some instances, the tobacco product is a combustible tobacco product. A representative combustible tobacco product is a cigarette. Suitable packaging is known for the various types of tobacco products, and the treatment with bacteriophage does not affect the packaging of the tobacco product.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Bacteriophage P4

M4 was identified as a facultative anaerobe, Gram positive cocci. The P4 bacteriophage was isolated and concentrated by Micreos BV (The Netherlands). P4 was then submitted to University of Nebraska-Lincoln for complete sequence identification. The nucleic acid sequence of P4 shows about 80% sequence identity to the nearest phage relative, phiP68, which is a *Staphylococcus aureus* bacteriophage and has a genome size of 18,277 bp.

The endolysin polypeptide sequence and the nucleic acid sequence encoding the endolysin from P4 are shown below.

```
                                              (SEQ ID NO: 1)
atgggaaaacaatatttaggaaagtggaacggtgtacccgtttatacc gattacttaccttatggtacaagacgtcccggcagaaagttatcaaca ggtaaacctgttttcgccgttgcacacgatacaggcaacttaaattca acagcacagcagaatgttaattttttatcgtaatacttacaatgagcaa ttcaatattgcttcagctcacttttttgtagatgataaagaatgtgtg atctgcattccgattgatgaggtcgcttatcatgtattacctgcagca cctatggataacgcttggtatgggcatgacgccaattatgcagcattc ggcggtgaagcatgttatttcagcgataaacaaaaatcacaaaaatca ttggataatttctgtcgtgtcatggcagcattatgcaaatcatggaat atcaacccggttaatcgtatgcccggtcatcaacaaattcaatttgat aaacaagacccccggcaacttgcttgcagcatgcggatatgaccgtaat
```

```
                                    -continued
gctatgcatattatagataatttagttgtcaaatatatgcagaacgcc aacactaaagttaaaaaatatatatttacaactggaaaggtaaatttaca gcgcataaagataatgatgaccctattgttgtcagaacaacaccgggt atgaatggtaaaattgtagaaaaaaacagctggattaaaccggggggaa tacgtaccattcgatcaaatcattaaaaaagacggttattggtggtta cgtttcaaatatgtacaaaaaggttcatctaaaaatgactttatatc cctatcggaaaaattgaagaaaaacatgaacgtattaagaacgaaaaa aatctatggggtaaactggaggtggaataa
```

```
                                              (SEQ ID NO: 2)
MGKQYLGKWNGVPVYTDYLPYGTRRPGRKLSTGKPVFAVAHDTGNLNS

TAQQNVNFYRNTYNEQFNIASAHFFVDDKECVICIPIDEVAYHVLPAA

PMDNAWYGHDANYAAFGGEACYFSDKQKSQKSLDNFCRVMAALCKSWN

INPVNRMPGHQQIQFDKQDPGNLLAACGYDRNAMHIIDNLVVKYMQNA

NTKVKKYIYNWKGKFTAHKDNDDPIVVRTTPGMNGKIVEKNSWIKPGE

YVPFDQIIKKDGYWWLRFKYVQKGSSKNDFYIPIGKIEEKHERIKNEK

NLWGKLEVE
```

The P4 endolysin polypeptide sequence exhibits about 62% sequence identity to a N-acetylmuramoyl-L-alanine amidase from *Staphylococcus epidermidis* VCU118 (GenBank Accession No. EHR86787.1) over about 68% of the P4 sequence. In addition, the P4 endolysin polypeptide sequence exhibits about 61% sequence identity to a N-acetylmuramoyl-L-alanine amidase from *Fusobacterium sp.* 3_1_27 (GenBank Accession No. ZP_06751371.1) over about 67% of the P4 sequence, and also exhibits about 59% sequence identity to N-acetylmuramoyl-L-alanine amidase from *Staphylococcus pseudintermedius* HKU10-03 (GenBank Accession No. YP_004149412.1) over about 100% of the P4 sequence.

Example 2—Isolation of Additional Bacteriophages from Tobacco

Eight different moist smokeless tobacco products and tobacco materials were used to isolate bacteriophages in addition to P4. 30 grams of the solid tobacco samples was added to 270 g of the low salt (5%) diluent in a filtered stomacher bag. The sample was mixed using a stomacher for 3 minutes at 200 RPM. The sample was then poured from the filtered side of the stomacher bag into a centrifuge tube and centrifuged for 30 minutes at 11,000 xg. The supernatant was poured off and passed sequentially through a 0.45 micron and 0.22 micron filter. The sterile filtrate was subjected to ultracentrifugation. 15 ml of the filtrate was added to the Amicon Ultra-15 Centrifugal Filter Device. The devices were centrifuged for 30 minutes at 1,500 xg to concentrate and separate the phages from the filtrate. 15 ml of the filtrate was then concentrated to 250 to 500 µl.

The filtrates were then combined 1:1 with 2× Tryptic Soy Broth (TSB), 2× low salt broth, 2× high salt broth, 2×15% salt broth (pH 8), 2×10% salt broth (pH 9 and pH 7.4). Each of the filtrate broth combinations, now referred to as enrichments, were then inoculated with 1 ml of a turbid culture of interest; *Marinilactibacillus*, *Virgibacillus*, and *Corynebacterium* were separately inoculated into each of the enrichments and incubated for 2 weeks, 1 week, or 2 days respectively. 2 ml of the enrichment was removed after incubation and centrifuged for 1 minute at 13,000 RPM. The supernatant was passed through a sterile 0.22 micron filter and placed into a sterile microcentrifuge tube. 10 µl of the sterile filtrates were then dropped on to the appropriate agars with the corresponding soft agars on top. The soft agars contained 100 µl of the appropriate culture for which it was enriched. The spot plates were left to absorb into the agar and then incubated at 32° C. until clear lysis zones developed. The enrichments were placed back into the incubator and processed 4 to 6 more times as stated above before the enrichment series was stopped.

Upon observation of a clear lysis zone (plaque), the plate was removed from the incubator and the plaque was harvested for isolation. A 1000 µl tip was placed over the plaque and gently dug into the soft agar overlay of the plate. The soft agar plug was then placed into 1 ml of SM buffer and refrigerated at 4° C. overnight to allow for diffusion of the bacteriophage. 10 µl of the SM buffer containing the phage was then dropped onto the appropriate soft agar with the appropriate strain in the soft agar. The plate was then incubated at 32° C. to confirm lysis of the bacterial strain.

Several bacteriophage were identified that are specific against the M5, M6 and *Geobacillus* bacteria.

Example 3—Titering P4

P4 was diluted in fresh SM Buffer using serial 1/10 dilutions to $10^{-8}$. 100 µl of P4 was transferred into 900 µl of sterile water in sterile microcentrifuge tubes. Each dilution was inverted 3 times by hand before the next dilution was performed. Brain Heart Infusion (BHI) agar was used as the base agar, with BHI soft agar as the overlay at a concentration of 4 g agar/L. 100 µl of freshly grown *Staphylococcus* was added to 4 ml of the BHI soft agar and gently vortexed. The soft agar/*Staphylococcus* mixture was gently poured over the BHI base agar and the swirled gently to allow the soft agar to evenly spread across the BHI agar in the petri plate. 10 µl of each dilution was dropped onto the BHI agar with a 4% BHI soft agar overlay to constitute a spot plate. The spot plate was allowed to dry for 30 minutes. The spot plate was transferred to 32° C. and incubated right-side up overnight to allow for plaque formation. The plates were removed after overnight incubation and observed for plaque formation.

The same procedure was used on *S. carnosus*, a test strain that was used by Micreos BV for propagation of P4. The procedure was also performed on low salt agar (5% salt) with low salt (5% salt) top agar to ensure no difference between BHI and low salt agars.

These experiments demonstrated that the bacteriophage shows specificity towards the genus of *Staphylococcus*, and high specificity towards the target strain M4. These experiments also show an estimation of the titer of P4. The phage was provided at $1.5 \times 10^{11}$, and the phage was shown to be effective against M4 at a concentration of $1.5 \times 10^7$. See FIG. 1.

Example 4—Enumeration of *Staphylococcus* in Tobacco in the Presence of P4

Tobacco that had been inoculated with *Staphylococcus* as explained above was used to enumerate *Staphylococcus* and P4. The tobacco samples were prepared by diluting tobacco samples through $10^{-5}$ with low salt (5% salt) diluent or high salt (18% salt) diluent. 30 grams of the tobacco sample was added to 270 g of the appropriate diluent in a filtered stomacher bag. The sample was mixed using a stomacher for 3 minutes at 200 RPM. The sample was then serially diluted by pulling sample from the filtered side of the stomacher bag. 100 µl of the tobacco sample was added to the appropriate soft agar (low or high salt), as well as 100 µl of P4, and gently vortexed. The soft agar was poured over the appropriate agar (low or high salt). 50 µl of each tobacco sample dilution series was spiral plated onto low or high salt agar. Once the spiral plated sample had absorbed into the agar, 100 µl of the P4 phage ($1.5 \times 10^9$) was spread plated over the agar. No soft agar was used in this preparation. The plates were incubated for either 7 days (low salt agar) or 8 weeks (high salt agar) at 32° C.

Figure 2:
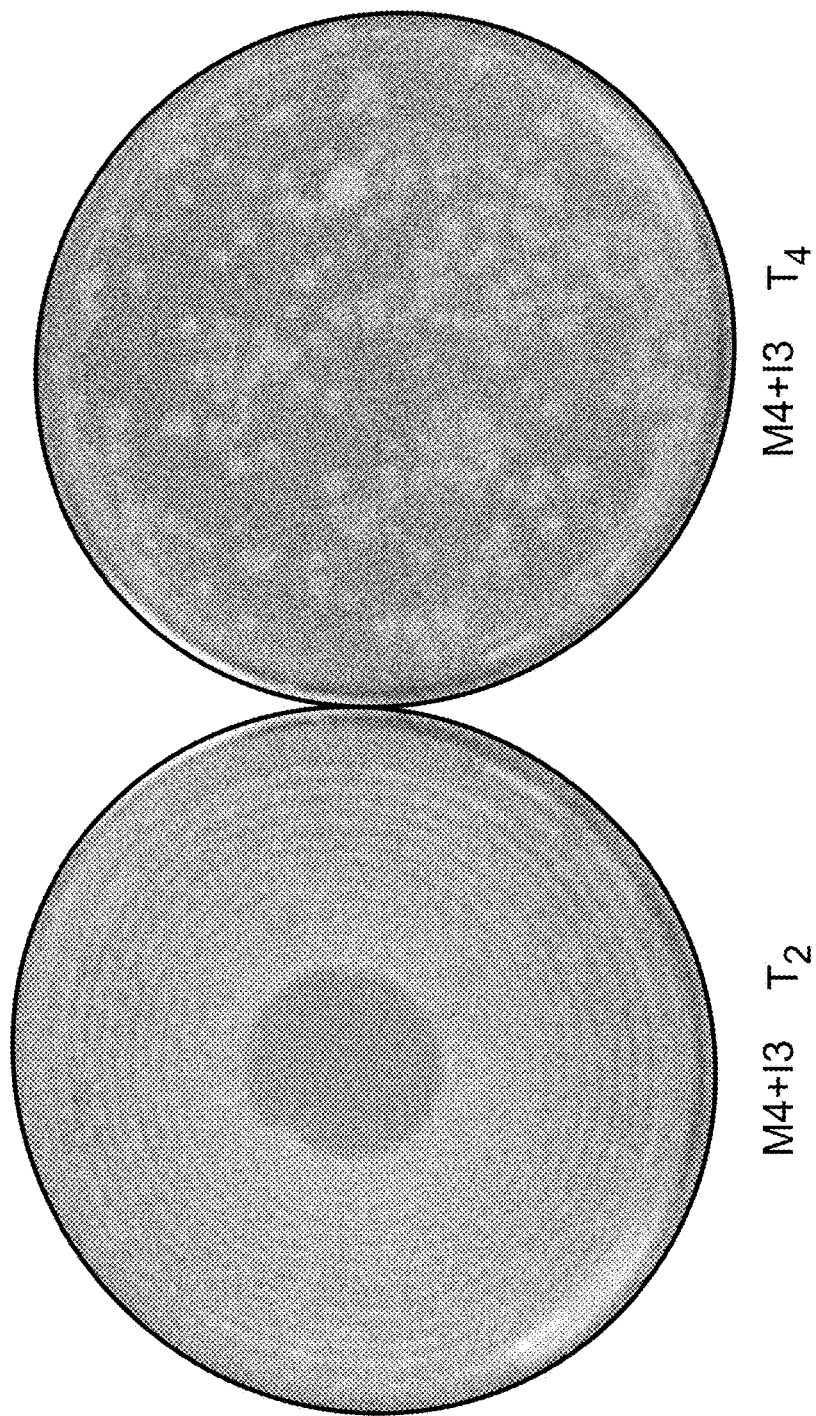
FIG. 2 shows a lawn of M4 from tobacco (left plate) and a lawn of M4 from tobacco in the presence of P4 (right plate) grown for 7 days in low salt agar.
Figure 3:
FIG. 3 shows a lawn of M4 from tobacco (left plate) and a lawn of M4 from tobacco in the presence of P4 (right plate) grown for 8 weeks in high salt agar.
Figure 3:
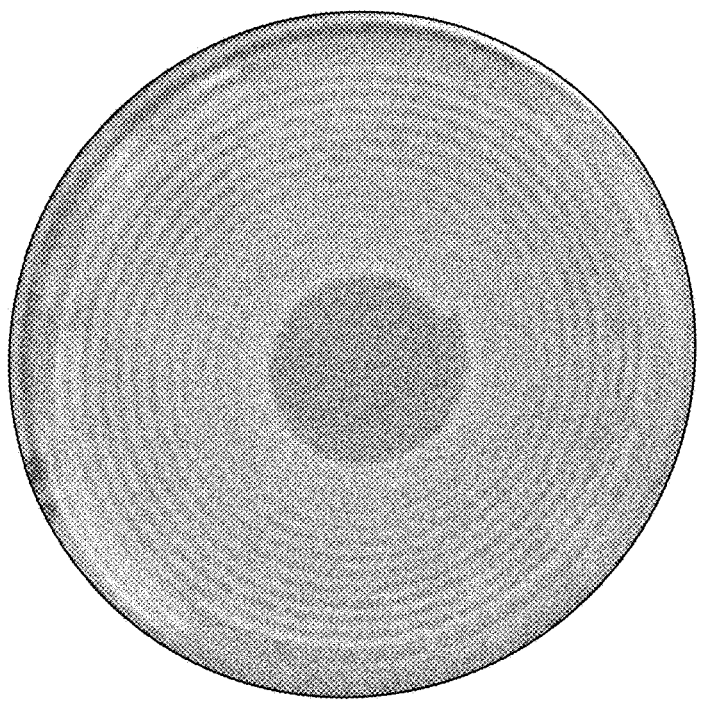

Results are shown in FIG. 2 and FIG. 3, and demonstrate that P4 is effective against *Staphylococcus* that was inoculated into the tobacco samples. This also shows efficacy of P4 on the high salt agar. Furthermore, the figures show that spreading the phage onto the surface allows for lysis of the target bacterium without the use of top agar overlays.

Example 5—Bacteriophage Application in Moist Smokeless Tobacco

The tobacco was inoculated with *Staphylococcus* sp., with a final concentration of $1.32 \times 10^6$ cfu/g (log 6.25). Bacteriophage P4 was added to tobacco at a final concentration of $9.93 \times 10^9$ pfu/g (log 9.99). The tobacco was mixed for three minutes on medium speed using a kitchen aid mixer to ensure complete mixing and contact of the bacteria and the phage. The tobacco was incubated at 35° C. for multiple weeks. P4 was again added to the tobacco using the same methods after incubation, at a final concentration of $5 \times 10^7$ pfu/g. *Staphylococcus* was not added after incubation.

Figure 4:
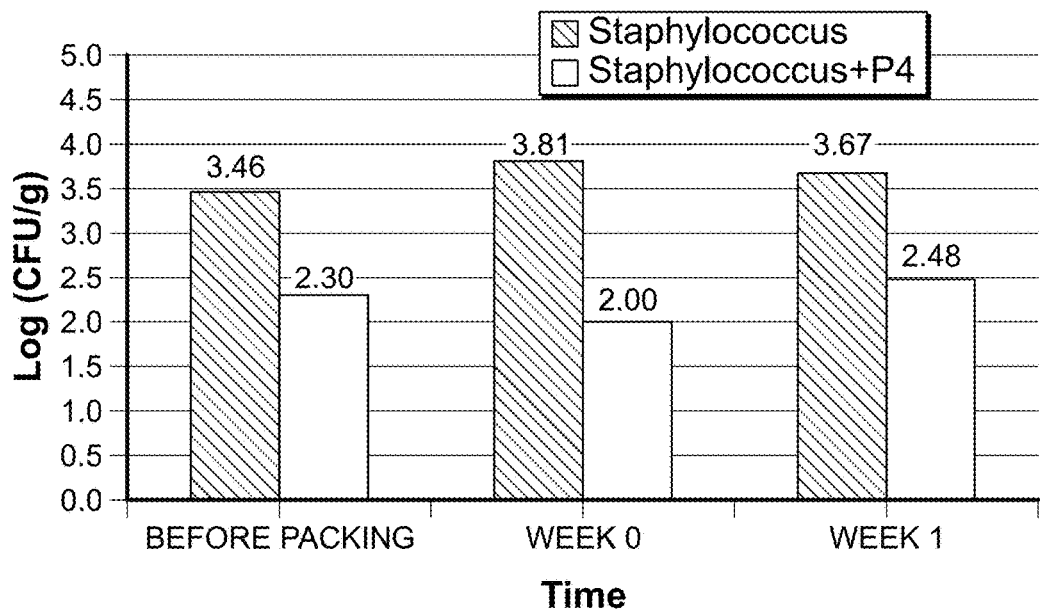
FIG. 4 is a graph showing the *Staphylococcus* load after incubation and addition of P4 before and after incubation.

The tobacco samples were monitored for growth of *Staphylococcus* during incubation and after incubation, and the results demonstrated that the use of P4 could inhibit the growth of *Staphylococcus* for up to 3 weeks in the can. P4 inhibited *Staphylococcus* by over log 1 at each time point. See FIG. 4.

Figure 5:
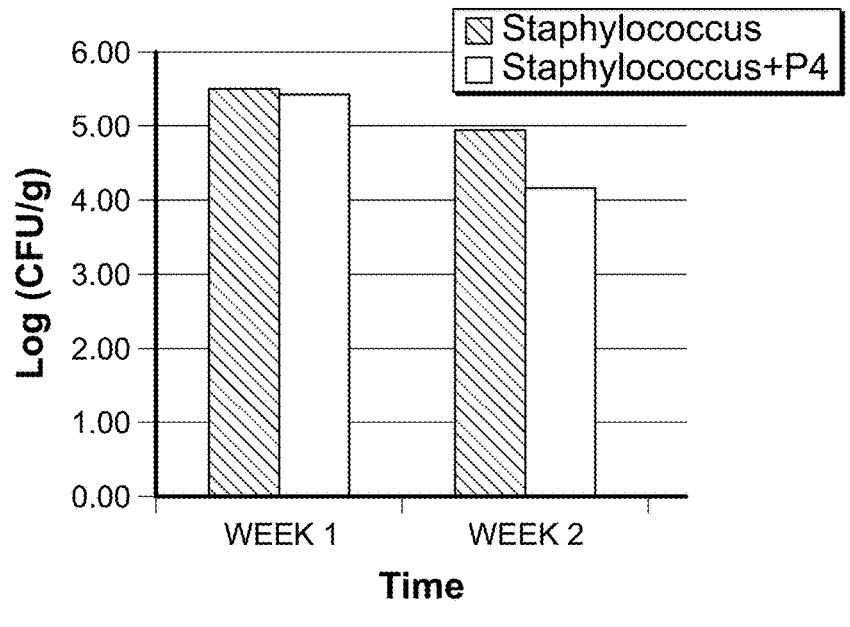
FIG. 5 is a graph showing moist, smokeless tobacco after inoculation with *Staphylococcus* and the addition of P4, followed by packaging in a fiberboard can. The use of P4 could inhibit the growth of *Staphylococcus* for over 2 weeks in the can.
Figure 6:
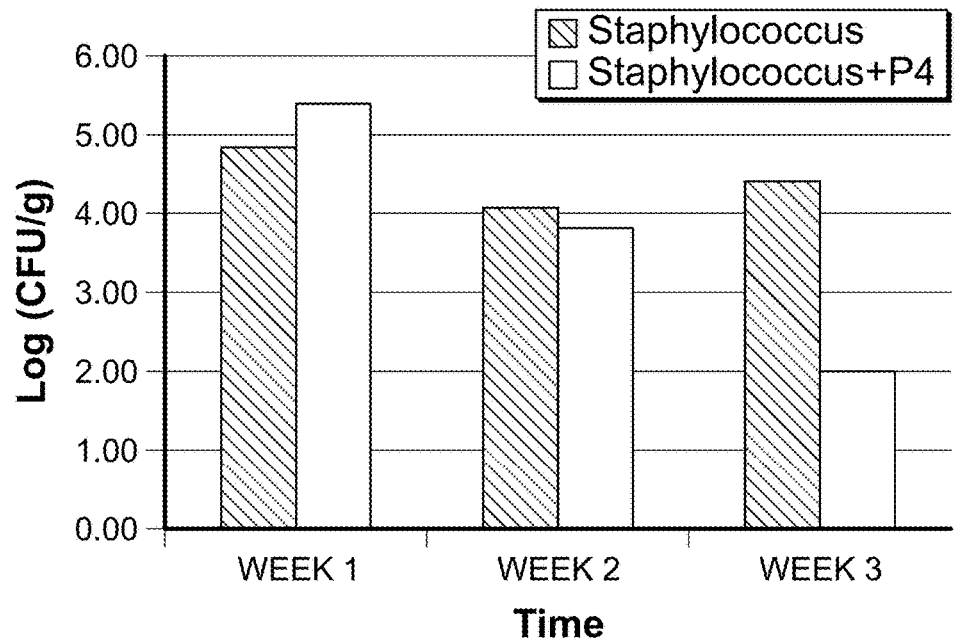
FIG. 6 is a graph showing moist, smokeless tobacco after inoculation with *Staphylococcus* and addition of P4, followed by packaging in ajar.

P4 was also added only to the tobacco after incubation. P4 was again added to the tobacco using the same methods after incubation, at a final concentration of $6.90 \times 10^7$ pfu/g (log 7.84). *Staphylococcus* was added after incubation at a final concentration of $6.07 \times 10^6$ cfu/g (log 6.01). The tobacco samples were monitored for growth of *Staphylococcus* for 3 weeks after packing in fiberboard cans (FIG. 5) and jars (FIG. 6). Results demonstrated that *Staphylococcus* was inhibited by P4 over two weeks in the fiberboard can. By week 3, the inhibition of *Staphylococcus* by P4 was greater than log 2. *Staphylococcus* was also inhibited in the jars by week 3. At week 3, the inhibition of *Staphylococcus* by P4 also was over log 2.

Example 6—Use of Bacteriophage in Reconstituted Leaf

*Geobacillus stearothermophilus* is a biofilm-producing bacterial organism that is obligately thermophilic and facultatively anaerobic. When it produces a biofilm on tobacco (e.g., reconstituted leaf), the congealed material interferes with the further processing of the tobacco. This is the first report of a *Geobacuillus stearothermophilus* forming a biofilm on tobacco.

A bacteriophage was isolated and concentrated by Micreos BV using the methods described above.

Figure 7:
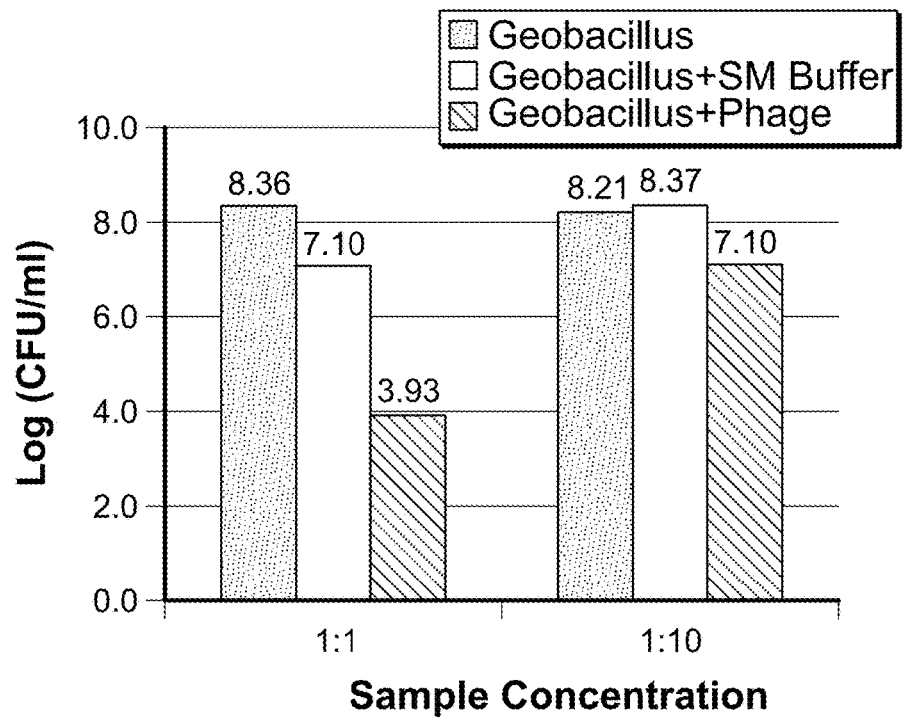
FIG. 7 is a graph showing the effect of various concentrations of Pgeo phage on *Geobacillus*.

To determine the effectiveness of the Pgeo phage, *Geobacillus stearothermophilus* was inoculated into fresh TSBYE (1/10) (Tryptic Soy Broth (TSB) with Yeast Extract (YE), the preferred broth of *Geobacillus stearothermophilus*) and incubated at 53° C. for up to four hours (OD between 0.5 and 0.9). The culture was then inoculated into fresh TSBYE containing either 1:1 or 1:10 ratio of Phage: TSBYE, SM Buffer:TSBYE (negative control), and TSBYE. The mixtures were incubated at 53° C. overnight and then serially diluted 1/10 to $10^{-5}$, and plated in duplicate on Tryptic Soy Agar with Yeast Extract (TSAYE). The plates were incubated at 60° C. overnight. The addition of the phage inhibited the growth of *Geobacillus stearothermophilus* by greater than log 3. Results are shown in FIG. 7.

Figure 8:
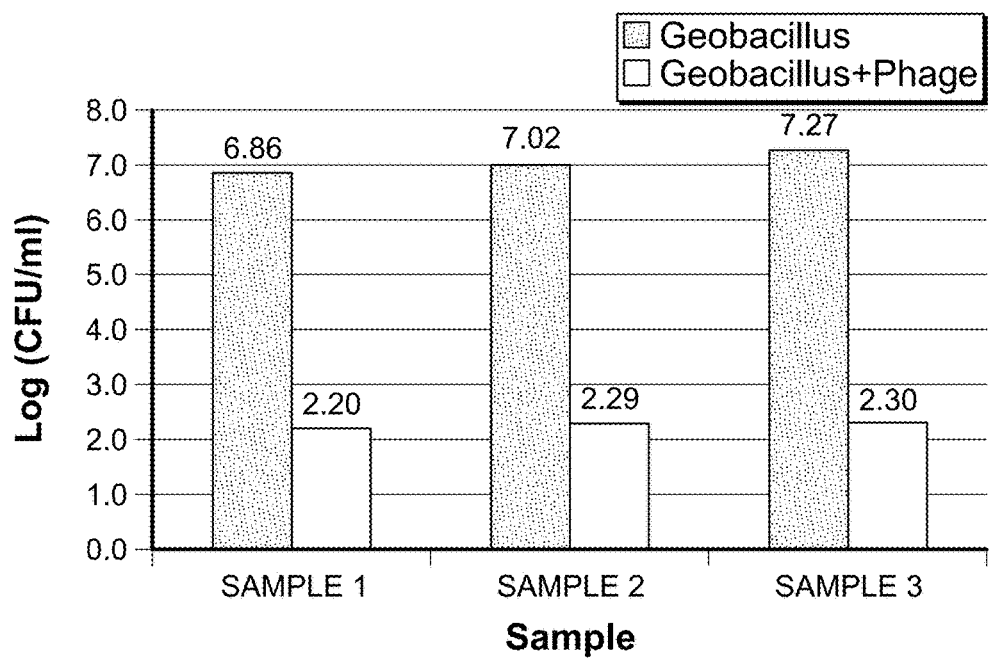
FIG. 8 is a graph showing the effect of Pgeo phage on *Geobacillus* in three samples of sterile reconstituted leaf (RL).
Figure 9:
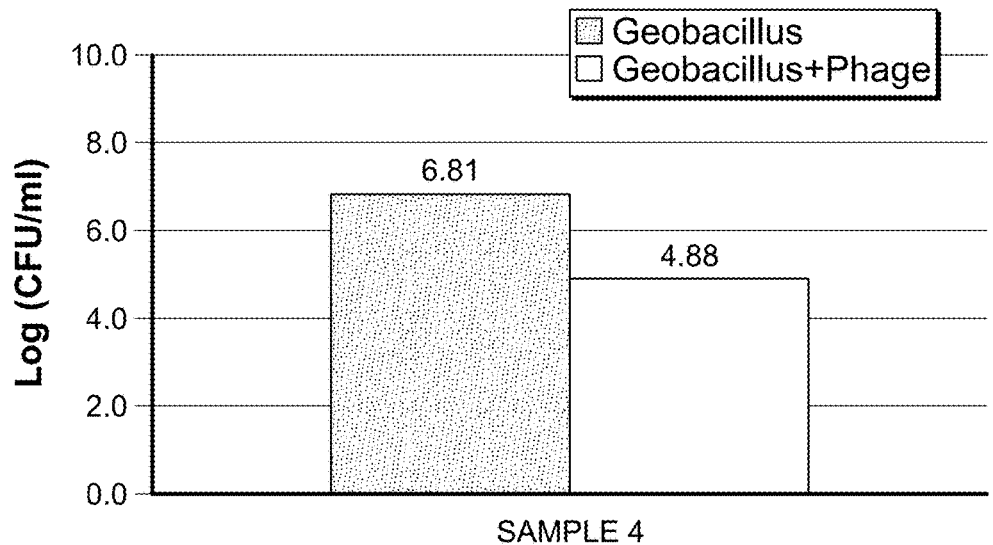
FIG. 9 is a graph showing the effect of Pgeo phage on *Geobacillus* in a fourth sample of sterile reconstituted leaf (RL).

Samples from the reconstituted leaf process were collected and stored at 4° C. (native) or sterilized by passing sequentially through 0.45 micron and 0.22 micron filters and stored at 4° C. (sterile). The samples were then inoculated with mid-log phase *Geobacillus stearothermophilus* as described above, SM buffer (negative control) or the bacteriophage. The samples were also supplemented with TSBYE to allow for growth. The mixtures were incubated at 53° C. overnight and then serially diluted 1/10 to $10^{-5}$, and plated in duplicate on TSAYE. The plates were incubated at 60° C. overnight. Results showed that the phage inhibited the growth of *Geobacillus stearothermophilus* by up to log 5. Results are shown in FIG. 8 and FIG. 9.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A tobacco product comprising an effective amount of a composition, wherein the composition comprises a bacteriophage comprising a nucleic acid sequence encoding an endolysin, wherein the endolysin comprises at least 95% sequence identity to the amino acid sequence shown in SEQ ID NO: 2, and wherein the effective amount is an amount of the bacteriophage that is sufficient to reduce the number of a viable bacteria in the tobacco product relative to a tobacco product in the absence of the composition.

2. The tobacco product of claim 1, wherein the nucleic acid sequence has at least 98% sequence identity to the nucleic acid sequence shown in SEQ ID NO: 1.

3. The tobacco product of claim 1, wherein the nucleic acid sequence has at least 99% sequence identity to the nucleic acid sequence shown in SEQ ID NO: 1.

4. The tobacco product of claim 1, wherein the nucleic acid sequence has the nucleic acid sequence shown in SEQ ID NO: 1.

5. The tobacco product of claim 1, wherein the endolysin has at least 98% sequence identity to the amino acid sequence shown in SEQ ID NO: 2.

6. The tobacco product of claim 1, wherein the endolysin has at least 99% sequence identity to the amino acid sequence shown in SEQ ID NO: 2.

7. The tobacco product of claim 1, wherein the endolysin has the amino acid sequence shown in SEQ ID NO: 2.

8. A tobacco product comprising a polypeptide having at least 95% sequence identity to the amino acid sequence shown in SEQ ID NO: 2.

9. The tobacco product of claim 8, wherein the polypeptide has at least 98% sequence identity to the amino acid sequence shown in SEQ ID NO: 2.

10. The tobacco product of claim 8, wherein the polypeptide has at least 99% sequence identity to the amino acid sequence shown in SEQ ID NO: 2.

11. The tobacco product of claim 8, wherein the polypeptide has the amino acid sequence shown in SEQ ID NO: 2.

* * * * *

SEQUENCE LISTING

```
<160> NUMBER OF SEQ ID NOS: 2

<210> SEQ ID NO 1
<211> LENGTH: 894
<212> TYPE: DNA
<213> ORGANISM: Artificial Sequence
<220> FEATURE:
<223> OTHER INFORMATION: synthetic oligonucleotide

<400> SEQUENCE: 1
atgggaaaac aatatttagg aaagtggaac ggtgtacccg tttataccga ttacttacct      60
tatggtacaa gacgtcccgg cagaaagtta tcaacaggta aacctgtttt cgccgttgca     120
cacgatacag gcaacttaaa ttcaacagca cagcagaatg ttaatttta tcgtaatact     180 tacaatgagc aattcaatat tgcttcagct cactttttg tagatgataa agaatgtgtg     240
atctgcattc cgattgatga ggtcgcttat catgtattac ctgcagcacc tatggataac     300
gcttggtatg ggcatgacgc caattatgca gcattcggcg gtgaagcatg ttatttcagc     360
gataaacaaa aatcacaaaa atcattggat aatttctgtc gtgtcatggc agcattatgc     420
aaatcatgga atatcaaccc ggttaatcgt atgcccggtc atcaacaaat tcaatttgat     480
aaacaagacc ccggcaactt gcttgcagca tgcggatatg accgtaatgc tatgcatatt     540
atagataatt tagttgtcaa atatatgcag aacgccaaca ctaaagttaa aaaatatatt     600
tacaactgga aaggtaaatt tacagcgcat aaagataatg atgaccctat tgttgtcaga     660
acaacaccgg gtatgaatgg taaaattgta gaaaaaaaca gctggattaa accgggggaa     720
tacgtaccat tcgatcaaat cattaaaaaa gacggttatt ggtggttacg tttcaaatat     780
gtacaaaaag gttcatctaa aaatgacttt tatatcccta tcggaaaaat tgaagaaaaa     840
catgaacgta ttaagaacga aaaaaatcta tggggtaaac tggaggtgga ataa           894

<210> SEQ ID NO 2
<211> LENGTH: 297
<212> TYPE: PRT
<213> ORGANISM: Artificial Sequence
```

```
<220> FEATURE:
<223> OTHER INFORMATION: synthetic peptide

<400> SEQUENCE: 2

Met Gly Lys Gln Tyr Leu Gly Lys Trp Asn Gly Val Pro Val Tyr Thr
1               5                   10                  15

Asp Tyr Leu Pro Tyr Gly Thr Arg Arg Pro Gly Arg Lys Leu Ser Thr
                20                  25                  30

Gly Lys Pro Val Phe Ala Val Ala His Asp Thr Gly Asn Leu Asn Ser
            35                  40                  45

Thr Ala Gln Gln Asn Val Asn Phe Tyr Arg Asn Thr Tyr Asn Glu Gln
        50                  55                  60

Phe Asn Ile Ala Ser Ala His Phe Val Asp Asp Lys Glu Cys Val
65                  70                  75                  80

Ile Cys Ile Pro Ile Asp Glu Val Ala Tyr His Val Leu Pro Ala Ala
                85                  90                  95

Pro Met Asp Asn Ala Trp Tyr Gly His Asp Ala Asn Tyr Ala Ala Phe
                100                 105                 110

Gly Gly Glu Ala Cys Tyr Phe Ser Asp Lys Gln Lys Ser Gln Lys Ser
            115                 120                 125

Leu Asp Asn Phe Cys Arg Val Met Ala Ala Leu Cys Lys Ser Trp Asn
        130                 135                 140

Ile Asn Pro Val Asn Arg Met Pro Gly His Gln Gln Ile Gln Phe Asp
145                 150                 155                 160

Lys Gln Asp Pro Gly Asn Leu Leu Ala Ala Cys Gly Tyr Asp Arg Asn
                165                 170                 175

Ala Met His Ile Ile Asp Asn Leu Val Val Lys Tyr Met Gln Asn Ala
                180                 185                 190

Asn Thr Lys Val Lys Lys Tyr Ile Tyr Asn Trp Lys Gly Lys Phe Thr
            195                 200                 205

Ala His Lys Asp Asn Asp Asp Pro Ile Val Val Arg Thr Thr Pro Gly
        210                 215                 220

Met Asn Gly Lys Ile Val Glu Lys Asn Ser Trp Ile Lys Pro Gly Glu
225                 230                 235                 240

Tyr Val Pro Phe Asp Gln Ile Ile Lys Lys Asp Gly Tyr Trp Trp Leu
                245                 250                 255

Arg Phe Lys Tyr Val Gln Lys Gly Ser Ser Lys Asn Asp Phe Tyr Ile
                260                 265                 270

Pro Ile Gly Lys Ile Glu Glu Lys His Glu Arg Ile Lys Asn Glu Lys
            275                 280                 285

Asn Leu Trp Gly Lys Leu Glu Val Glu
            290                 295
```